United States Patent [19]

Nilson

[11] 4,236,516
[45] Dec. 2, 1980

[54] SYRINGE AND DISPOSABLE CONTAINER THEREFOR

[76] Inventor: Nils B. Nilson, Finnstugatan 30, Mjölby, Sweden, S-59500

[21] Appl. No.: 878,267

[22] Filed: Feb. 16, 1978

Related U.S. Application Data

[63] Continuation of Ser. No. 684,020, May 7, 1976, abandoned.

[51] Int. Cl.$^3$ .............................................. A61M 5/24
[52] U.S. Cl. .............................. 128/216; 128/218 D; 128/234; 222/95; 222/107; 222/215
[58] Field of Search .............. 128/215, 216, 218, 234, 128/219, 232, 2 F, 275–278, DIG. 5; 222/95, 105, 107, 215, 386.5, 389; 73/425.6; 141/2, 23–25, 27, 357; 417/550, 555 R

[56] References Cited

U.S. PATENT DOCUMENTS

| | | | |
|---|---|---|---|
| 798,093 | 8/1905 | Dean | 128/216 |
| 921,130 | 5/1909 | Lockwood | 128/DIG. 5 |
| 2,595,493 | 5/1952 | Slaby et al. | 128/276 X |
| 2,688,964 | 9/1954 | Smith | 128/216 |
| 2,695,023 | 11/1954 | Brown | 128/218 C |
| 2,915,986 | 12/1959 | Sisson | 417/550 X |
| 3,023,751 | 3/1962 | Lipsky et al. | 128/218 D |
| 3,111,145 | 11/1963 | Kerns | 128/278 X |
| 3,127,846 | 4/1964 | Kerns | 128/273 X |
| 3,161,194 | 12/1964 | Chapman | 128/218 R |
| 3,335,914 | 8/1967 | Strazdins et al. | 128/218 R |
| 3,699,961 | 10/1972 | Szpur | 128/218 M |
| 3,785,367 | 1/1974 | Fortin et al. | 128/2 F |
| 4,072,249 | 2/1978 | Ekemstam et al. | 128/232 X |
| 4,073,288 | 2/1978 | Chapman | 128/2 F |
| 4,131,217 | 12/1978 | Sandegren | 128/216 X |

FOREIGN PATENT DOCUMENTS

114199  3/1926  Switzerland .............. 128/216

*Primary Examiner*—Dalton L. Truluck
*Attorney, Agent, or Firm*—Finnegan, Henderson, Farabow, Garrett & Dunner

[57] ABSTRACT

In a syringe comprising a barrel and a plunger reciprocably mounted therein the end wall of the barrel at the discharge end thereof is formed by a disposable container removably attached to the barrel. A flexible wall portion of the container facing the plunger is moved towards and away from a rigid wall portion of the container by the reciprocating movement of the plunger in order to decrease and increase, respectively, the interior volume of the container.

18 Claims, 8 Drawing Figures

SYRINGE AND DISPOSABLE CONTAINER THEREFOR

This is a continuation of application Ser. No. 684,020, filed May 7, 1976, now abandoned.

BACKGROUND OF THE INVENTION

1. Field of the Invention

This invention relates to improvements in syringes for effecting subcutaneous and intramuscular injections of medicaments and the like into human beings and animals and for taking blood samples therefrom.

2. Description of the Prior Art

Most syringes now used in hospitals, offices and health centers are of the disposable type, that is, they are disposed of or discarded after one use. These syringes usually comprise two pieces—a barrel and a plunger or piston mounted for reciprocable movement in the barrel. Both parts are usually made of plastic material. The barrel has a nozzle at the discharge end for the attachment of a hypodermic needle or cannula. On the plunger a sealing ring of rubber material is provided to act as a seal between the plunger and the inside surface of the barrel. Either the barrel or the plunger is provided with a scale by which the volume of liquid drawn into or dispensed from the barrel may be accurately determined.

As a disposable product a syringe of this type, although made by modern mass production methods such as injection molding, is relatively expensive due to the materials and precision involved in the manufacture thereof. Considering the enormous number of disposable syringes used over the world each year, estimated at several billions, the cost and waste of materials is significant and can hardly be justified. Any reduction in the manufacturing cost of a syringe, even if it amounts to only a fraction of a cent, can provide a large saving. Consequently, great efforts have been made and still are being made to lower the manufacturing costs of disposable syringes.

These efforts have not so far resulted in a radical change of the construction or the method of manufacturing of disposable syringes. They are still constructed as a two piece article which has to be thrown away in its entirety after having been used only once.

It has not been suggested so far to limit the disposable aspect to part of the syringe only; a readily apparent problem in connection therewith is the difficulty to maintain in a satisfactory manner the sterility of the syringe if a part thereof is to be used more than once.

It has been proposed to combine a barrel and a plunger with a replaceable container positioned at the discharge end of the barrel, the container being introverted or collapsed upon itself in use by action of the plunger to eject or administer the medicament contained in the container. Syringes of this type are disclosed in U.S. Pat. No. 978,488 to Roesch dated Dec. 13, 1910 and in U.S. Pat. No. 2,514,575 to Hein dated July 11, 1950. However, in these prior art syringes the container is a prefilled closed cartridge or capsule which is positioned in the barrel. The barrel is closed at the discharge end by a continuation of the barrel or by a separate end cap or like element. A discharge opening is provided at the discharge end to communicate with the attached needle or cannula.

A problem with this type of syringe is the possible contamination of the reusable elements following discharge of the cartridge or capsule contents. The expended cartridge or capsule must be withdrawn from the rear of the barrel or the end cap must be disconnected to permit cartridge or capsule removal. In either case, any contact of unexpended medicament with the reusable elements requires that these elements be cleaned and then sterilized. Additionally this type of syringe only permits discharge of the container contents and does not allow the medicament or the like to be drawn into the container under sterile conditions. This is a problem also for the injection apparatus disclosed in U.S. Pat. No. 3,308,818 to Rutkowski dated Mar. 14, 1967 wherein a container is located in a barrel which functions as a gas expansion chamber, and the container is introverted upon itself by gas pressure produced in said barrel by an explosive device.

SUMMARY OF THE INVENTION

The present invention overcomes the foregoing problems and disadvantages of the prior art by providing a syringe in which only a small part of the apparatus is discarded after each use, the rest of the syringe being used repeatedly, and wherein this can be achieved while maintaining a high degree of sterility and without contamination of the reusable portion. Furthermore, the syringe of this invention finds utility either in administering or injecting medicaments or the like from the disposable container, or in collecting blood samples or other bodily fluids.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the syringe of this invention comprises a barrel and a plunger or piston reciprocable therein which are both to be used more than once, and a disposable discharge end portion providing a container, which is releasably connected with the barrel to be discarded after each use of the syringe.

More particularly the syringe according to the invention comprises an elongated barrel having a discharge end, a plunger reciprocably mounted in the barrel, a container, means for removably attaching the container to the discharge end of the barrel to form the end wall thereof, said container having a substantially rigid first wall portion at the exterior side of the end wall and having an inside surface, and a flexible second wall portion at the interior side of the end wall and introvertible upon the inside surface of the first wall portion, said plunger having an end surface facing the container and designed to contact said second wall portion during its reciprocable movement said end surface shaped to substantially conform to the shape of said inside surface of said first wall portion, and a nozzle on said first wall portion for attaching a hypodermic needle thereto.

The invention also provides a container to be used in a syringe of this type and a syringe system by which the containers may be stored under sterile conditions and may easily be attached to the barrel without contamination of the interior space of the container, as well as a method in operating the syringe according to the invention.

The accompanying drawings, which are incorporated in and constitute part of this specification, illustrate one embodiment of the invention and, together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings.

Figure 1:
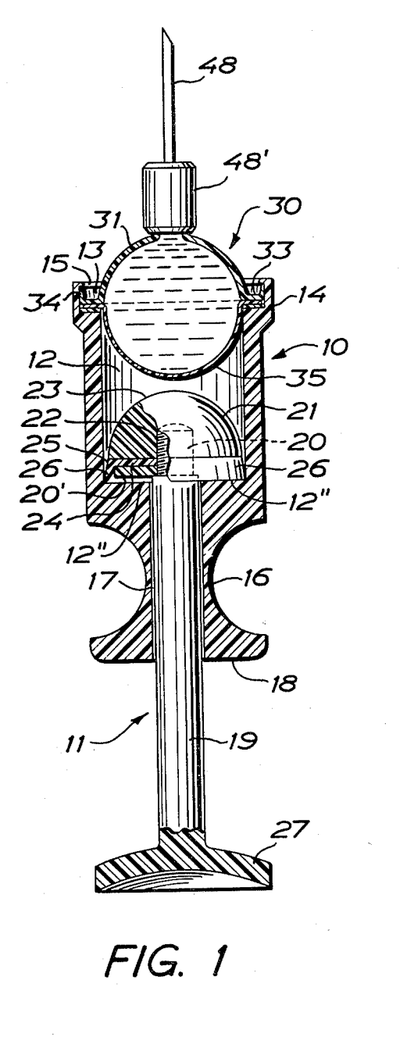
FIG. 1 is a side view partly in axial cross-section of the preferred embodiment of the syringe constructed according to the teachings of the invention, shown prior to the dispensing operation.
Figure 3:
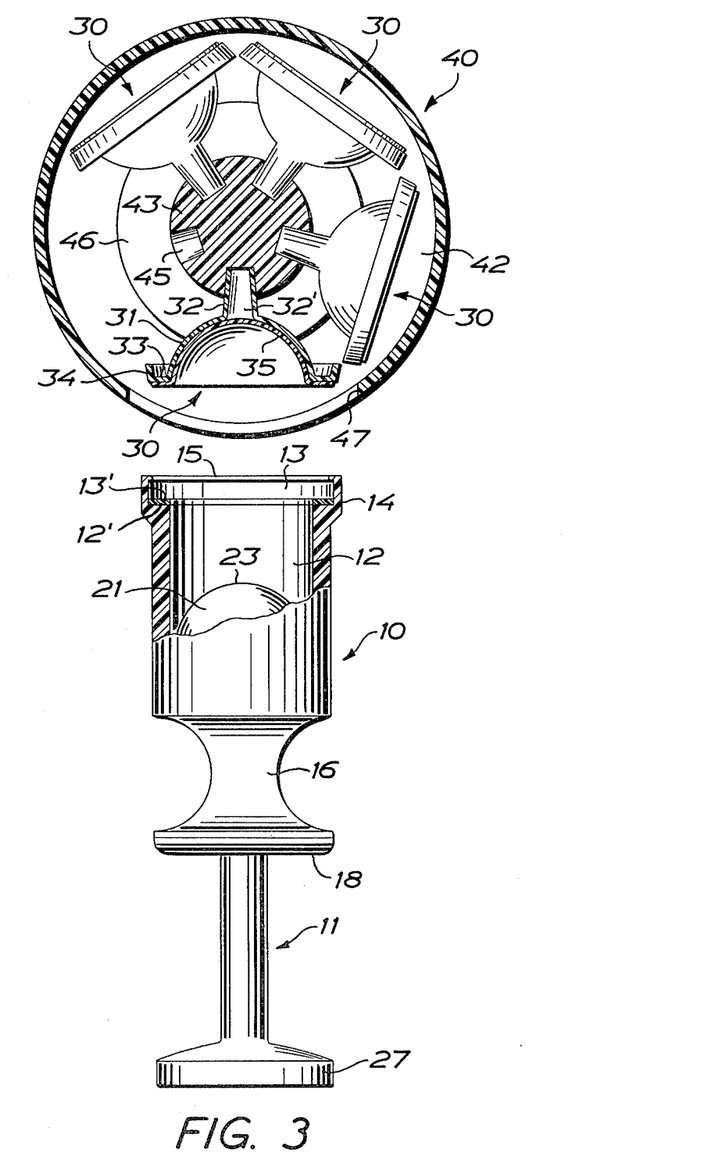
FIG. 3 is a plan view partly in cross-section of the preferred embodiment of a syringe system constructed according to the teachings of the invention comprising a barrel and a reciprocable plunger together with a magazine for storing under sterile conditions a large number of empty containers.

Referring to FIGS. 1 and 3 of the drawings which disclose in detail the construction of the syringe according to the teachings of the invention such syringe provides a two-part unit which is constructed for repeated use and comprises an elongated barrel 10 having a discharge end, and a plunger or piston 11 reciprocably mounted in the barrel. This barrel can be made as an integral element entirely of metal or a plastic material and preferably is made of a transparent plastic material.

The barrel forms a cylindrical cavity 12 which widens at a shoulder 12' into an enlarged cylindrical socket 13 at the discharge end of the barrel, said socket 13 being defined at is periphery by an integral wall 14. On the shoulder there is positioned an annular sealing ring 13'. At the edge of wall 14 there is formed on the inside surface thereof a circumferential, inwardly-directed rib or lip 15 preferably with a rounded profile. At the end opposite to the discharge end the barrel has a circumferential recess 16 having a concave or rounded shape which provides a finger grip by which the barrel may be grasped during the operation of the syringe. If desired, the bottom of the groove may be flattened.

The barrel forms a cylindrical passage 17 extending from the inner end or bottom 12" of cavity 12 through the finger grip portion 16 and opening at the flat end surface 18 of the barrel. Plunger 11 comprises a cylindrical rod 19 which is received in passage 17 and is slidable therein. Clearance is provided between plunger 11 and passage 17 to allow air to pass between cavity 12 and the surrounding atmosphere.

Rod 19 forms a threaded inner end 20 on which is mounted a plunger head 21, a threaded bottom hole 22 in the plunger head receiving the threaded end 20 of the rod. This plunger head also forms a hemispherical end surface 23 facing the discharge end at socket 13 of the barrel, and a flat base surface 24 facing the bottom 12" of the barrel. Against the base surface 24 there is applied to the plunger head a sealing element 25 of a soft rubber material such as silicone rubber. The sealing element is clamped between a washer 20' and the end surface of the plunger head and forms a conical lip or sleeve 26 which slopes outwardly and sealingly engages, due to the inherent elasticity thereof, the inside cylindrical surface of cavity 12. The sealing element also acts as a valve member during the expulsion step as later described. At the external end of rod 19 this rod forms a disc 27 integral with the rod for manually operating the plunger.

A container or cartridge constructed to be removably attached to the discharge end of the barrel to form the end wall thereof is generally indicated at 30 and comprises a substantially rigid hemispherical first wall portion 31 at the exterior side of the end wall and having an inside surface. Said first wall portion forms an externally protruding centrally positioned nozzle 32 conically tapered towards the outer end thereof, for attaching a hypodermic needle or cannula thereto.

Means for removably attaching the container to the discharge end of the barrel comprises a circumferential flange 33 on the container which merges into a conical rim 34, see FIG. 3, protruding outwardly in the same direction as nozzle 32 at one side of the flange. Said first wall portion 31 of container 30 may be made of a suitable plastic material. The container further comprises a flexible second wall portion 35 at the interior side of said end wall formed by the container when attached to the barrel. Said second wall portion is connected to the other side of flange 33 preferably by adhesive, melting or ultra sonic welding. Wall portion 35 preferably is made of a flexible plastic material. It is introvertible upon the inside surface of the first wall portion 31 to the collapsed position shown in FIG. 3, and in this position said second wall portion 35 is seen to be dimensioned and formed so as to contact the concave inside surface of wall portion 31 of the empty container, following the curvature of said wall portion. This is the condition in which the container is delivered.

In the collapsed condition, the interior of the container is accessible through the passage 32' of nozzle 32 and, therefore, the requirement of sterility is not met if the nozzle passage is left uncovered when the container is delivered. This passage has to be closed under sterile conditions and this is preferably made by delivering several containers in a magazine as shown in FIGS. 3 and 4.

Figure 4:
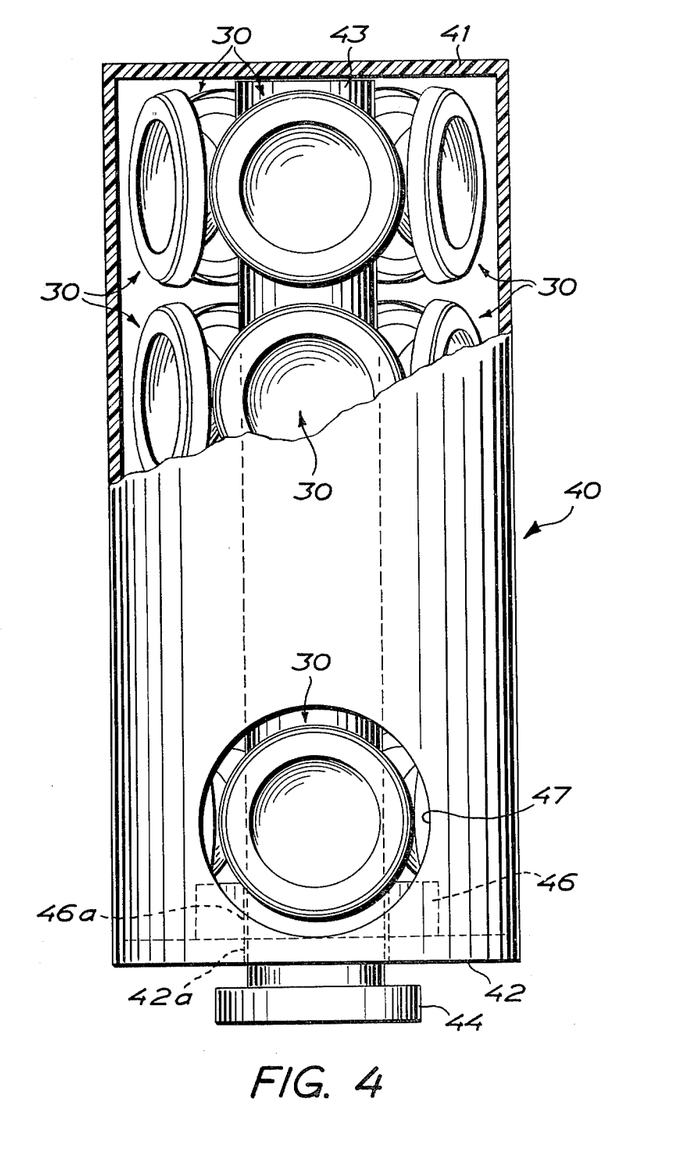
FIG. 4 is a side view, partly in cross-section of the magazine shown in FIG. 3.

Referring to FIGS. 3 and 4 there is provided a cylindrical housing 40 having a closed end wall 41 and an end wall 42 centrally apertured at 42a. A cylindrical stem 43 passing through aperture 42a of end wall 42 and being rotatable and axially displaceable therein projects at one end thereof from the housing and is provided with a head 44 for the manipulation of the stem. Several annular sets of radial conical bottom holes 45 are formed in the stem at axially spaced levels thereof. These holes are each sized to receive nozzle 32 of a container 30 of the type described above and to permit retention of the nozzle by a slight press fit in the hole.

Thus, a plurality of empty containers are fitted to the stem arranged in axially spaced annular banks thereon, and in this position the interior of each container is closed from the surrounding. Consequently, the containers can be stored in this way in a sterile condition obtained e.g. by gamma radiation of the containers when fitted to the stem. The lowermost annular bank of containers rests against an apertured shoulder 46 formed centrally on the inside surface of wall 42, the aperture 46a thereof being in registry with aperture 42a, and in this position the stem may be rotated to bring each of the containers in the lowermost bank of containers separately opposite an opening 47 in the cylindrical side wall of the housing for access by the barrel socket 13.

When the lowermost annular bank of containers 30 has been removed from the magazine, stem 43 will be lowered so that the next annular bank of containers will bear on shoulder 46 on the apertured end wall 42 to support the stem and the containers attached thereto. In this way each annular bank of containers is brought to the level of opening 47 by axial displacement of stem 43 and when brought to this level each of the containers of the lowermost bank of containers can be removed separately from the magazine through opening 47.

Referring to FIG. 3 the removal of each container through opening 47 is effected by introducing barrel 10 at the discharge end thereof into opening 47 and by pushing socket 13 into flange 33 and rim 34 of the container which has been brought opposite opening 47 to receive the flange and rim in socket 13. When the barrel is being slid over rim 34 to receive the rim in socket 13 the rim flexes or gives when sliding against rib or lip 15 and then, after having slipped over the rib or lip, springs out automatically to engage at the edge thereof the inner side of the rib or lip. By the engagement thus obtained between the barrel and the container the container will be retained by the barrel and will be withdrawn from stem 43 by withdrawal of the barrel. A hypodermic needle or cannula 48 having a socket 48' may be forcefitted manually to nozzle 32 of container 30 connected with the barrel and, thus, a complete and operable syringe has been formed.

If the plunger head 21 is not already contacting the concave outside surface formed by wall portion 35 collapsed against and following the curvature of the inside surface of wall portion 31 it is displaced manually to such position to contact wall portion 35, the end surface of the plunger head being hemispherical to substantially conform to the inside surface of wall portion 35 when collapsed against wall portion 31. When the plunger head is being moved towards the container at the discharge end of the barrel, said end being closed off by the container forming an end wall of the barrel air enclosed in front of the moving plunger will pass between the plunger head and the cavity wall due to yielding of the conical lip or sleeve 26 of sealing element 25. The atmosphere communicates with the interior of the barrel through the clearance around rod 19 in passage 17.

Figure 2:
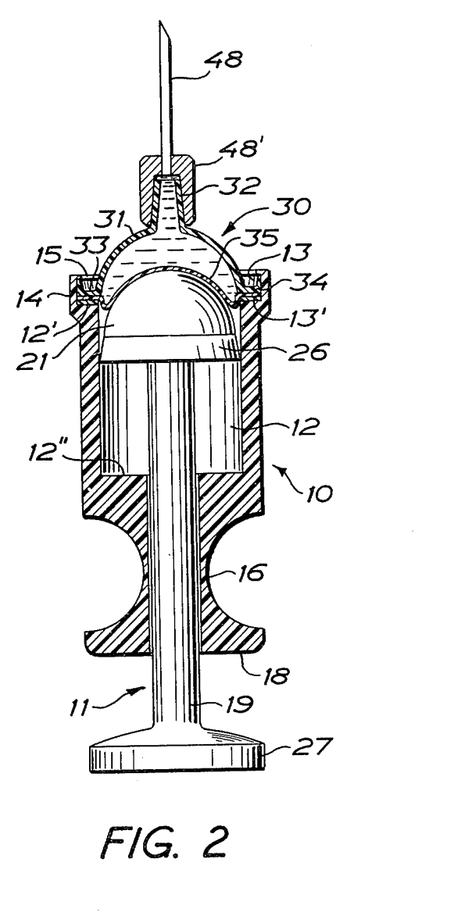
FIG. 2 is a view similar to FIG. 1 of the complete syringe, shown during the operation sequence.

Cannula 48 is then inserted in a bottle or the like containing a liquid medicament to be received by the container, or in a blood vessel in order to take a blood sample therefrom, as the case may be. As the plunger 11 is retracted the conical lip or sleeve 26 of sealing element 25 will sealingly engage the inside wall of the barrel due to the fact that it will be brought to expand towards that wall by the friction between the lip or sleeve and the wall. The part of cavity 12 enclosed between the plunger head and the inner end of the cavity is vented through the clearance formed around rod 19 in passage 17 so that no pressure builds up behind the plunger head. Thus, a subpressure (partial vacuum) will be created in cavity 12 between the plunger head and the end wall formed at the discharge end of the barrel by container 30 a leakproof seal being provided between the container and shoulder 12' by sealing ring 13'. No air will be able to pass into this space from the surrounding since an effective seal will be maintained also between plunger lip 26 and the inside surface of the barrel wall when the plunger is retracted from the discharge end as explained above. By the subpressure thus created wall portion 35 will be progressively withdrawn from wall portion 31 as shown in FIG. 2 and the container will be filled with liquid.

In operation, to eject the liquid from the container e.g. for adminstering the medicament or for transferring the blood sample to a test tube, as the case may be, the container is emptied by pressing the plunger head 21 against the filled container. During this operation needle 48 is inserted in a blood vessel or under the skin of a human being or an animal for administering the medicament, or alternatively in a test tube or other receiver to which the blood sample shall be transferred for treatment or test operations. The flexible wall portion 35 will be introverted mechanically by the hemispherical end surface 23 of plunger head 21 and will be collapsed against the inside surface of wall portion 31. No overpressure is allowed to build up in front of the plunger head due to the valve action provided by the lip or sleeve 26 of sealing element 25 as described above. This is one of the important features of the syringe system according to the invention. If air under pressure trapped between the container and the plunger head were allowed to pass into the container through a perforation in a defective flexible wall portion 35 the air could arrive in a blood vessel which could be dangerous to the patient and even mortally, or build up of compressed air in front of the plunger head could eject the container from socket 13 of the barrel. If liquid leaks into the cavity 12 of barrel 10 from a defective container it could be contaminated by contacting the barrel and the plunger. Such contaminated liquid will pass to the back side of the plunger head at lip 26 where the flow resistance is lower than that in the cannula, and thus will not be administered from the syringe. This is a further safety feature of the syringe according to the teachings of the invention.

When the liquid in the container has been expelled therefrom, the emptied container can be ejected from the barrel by means of the plunger. An increased force is exerted manually on the flexible wall portion 35 which contacts wall portion 31 when the container has been emptied, and under the force thus exerted on the emptied container rim 34 is brought to yield and to disengage rib or lip 15. The container is thrown away together with the cannula and a fresh container is attached to the barrel in the manner described. Thus it will be seen that only a small part of the complete syringe is provided as a disposable product to be thrown away after each use. This will considerably reduce the cost for each operation in relation to the common practice to throw away from each injection the entire syringe, thanks to the saving of material which also means that less waste has to be disposed of.

There may be provided on barrel 10 or on rod 19 a graduation or scale which is read against an index on the rod and the barrel, respectively, for reading the volume of liquid drawn into container 30. Since the operative connection between wall portion 35 of container 30 and the plunger or piston head 21 during the suction stroke of the syringe is provided by the subpressure created in front of the plunger between the plunger head and the container, the increase of the interior volume of the collapsed container when wall portion 35 is moved away from wall portion 31 will be the same volume as that displaced by plunger head 21 in the cylindrical cavity 12. This means that the graduation or scale will be linear.

It is possible to have containers of different size for co-operation with one and the same barrel so that a number of standard volumes can be chosen by choosing a container of the desired volume, although different sized barrels may be used for containers of different size. Other volumes than standard volumes may be determined by means of the graduation and the index against which such graduation is read.

Figure 5:
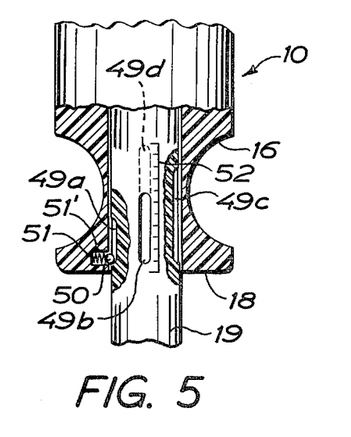
FIG. 5 is a fragmentary side view in cross-section of the syringe disclosing an embodiment for automatically controlling the amount of liquid to be drawn into or expelled from the syringe container.

FIG. 5 discloses an arrangement by which a container 30 can be filled with liquid to a predetermined extent without reading a graduation. In rod 19 there are provided four axially extending grooves 49a, 49b, 49c and 49d which are spaced apart ninety degrees about the axis of rod 19. These grooves are of different length and they have all the end adjacent disc 27 in a common transverse plane of the rod. A detent formed by a ball 50 is biased by a pressure spring 51 received by a cavity 51' formed in the barrel, the ball thus being pressed against rod 19. This rod may be rotated in passage 17 to bring one of the grooves into register with the ball. Such rotation takes place against the resistance offered by ball 50 when it is forced out of the groove in which it is received at the time, against the bias provided by spring 51. In FIG. 5 the ball is received by groove 49a. When the plunger is displaced axially the ball rides in the groove and offers increased resistance to movement beyond the ends of the groove to indicate the length of the stroke defined by the groove cooperating with the ball. When the plunger is being displaced for sucking liquid into the container attached to the barrel, the ends of the axial distance represented by a groove such as groove 49a will be felt as a pressure point at each end of the axial distance represented by the groove. The length of each groove may be adjusted to correspond to a predetermined volume of liquid in the container. If a greater volume is desired rod 19 may be rotated in order to bring the proper groove into register with ball 50. It is possible to adjust the volume by means of a graduation 52 provided on rod 19, end wall 18 of the barrel forming an index for reading such graduation, in case it is wanted to fill the container to an extent which does not correspond to one of the standard volumes represented by the grooves. The longest groove 49d should preferably correspond to complete filling of the container.

Figure 6:
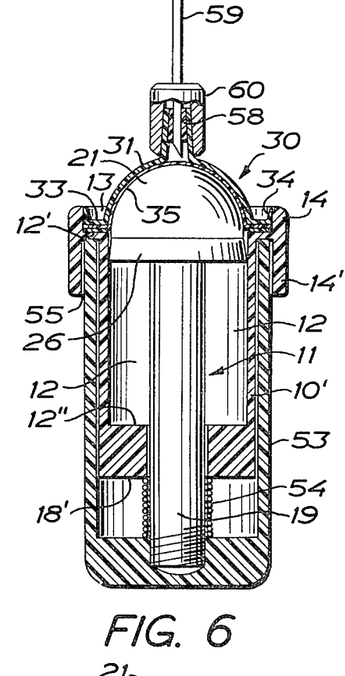
FIG. 6 is a cross-sectional view of a second embodiment of the syringe constructed according to the teachings of the invention for withdrawing blood samples or other liquids.
Figure 7:
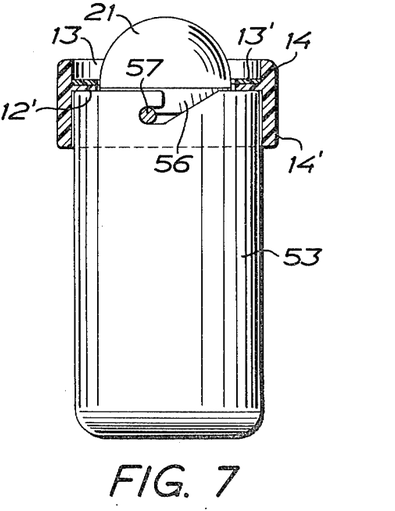
FIG. 7 is a side view of the syringe shown in FIG. 6 with the container removed.
Figure 8:
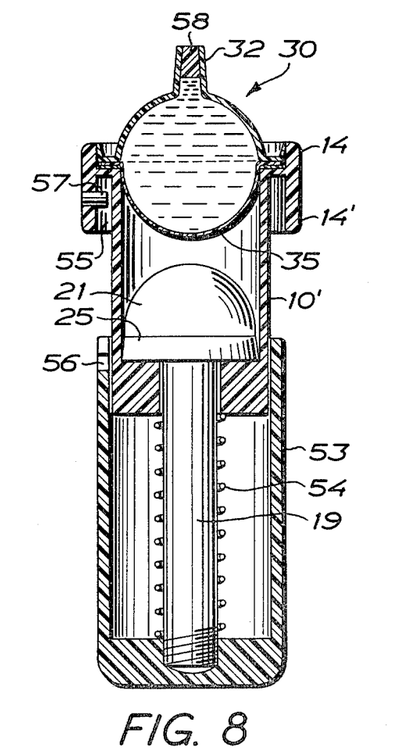
FIG. 8 is a sectional view of the syringe shown in FIG. 6 after a liquid sample has been extracted.

In FIG. 6 to 8 there is disclosed an embodiment of the invention which has been developed preferably to assist in taking blood samples from a human being or an animal. In this case there is provided on barrel 10' a socket or sleeve 53 having an open end. The barrel slides telescopically in and is received by this sleeve which at the other closed end is connected to the outer end of rod 19. Between the end surface 18' of the barrel and the bottom of sleeve 53 there is arranged a helical compressed spring 54 biasing the barrel and the sleeve to extend the barrel from the open end of the sleeve as disclosed in FIG. 8. As in the previous embodiment there is provided a socket 13 receiving flange 33 and rim 34 of a container 30 but in this case there is no rib such as rib 15 in FIGS. 1 to 3 provided on the inside surface of the side wall 14 of socket 13. Since the syringe in this embodiment of the invention is adapted for sucking liquid into the container when a blood sample is being taken but not for expelling the blood from the container when connected with the barrel the frictional engagement between rim 34 and the inside of wall 14 is sufficient to maintain the container on the barrel the more so as the subpressure created between the container and the plunger head when the plunger is withdrawn forces the container to be pressed against sealing ring 13' on shoulder 12'. Socket 13 is extended at 14' to form together with the rest of barrel 10' an annular groove 55 for receiving sleeve 53 as shown in FIG. 6, which can be brought to this position by displacing plunger head 21 towards the discharge end of barrel 10' by movement of the barrel within sleeve 53 against the action of spring 54 thereby compressing the spring. For arresting sleeve 53 in this position there is provided in the sleeve a notch 56 of the form disclosed in FIG. 7 and there is provided on socket extension 14' a pin 57 extending radially inwardly which may be brought into engagement with notch 56 by introducing the pin into the notch when sleeve 53 is pressed against the discharge end of barrel 10' and then rotating the sleeve so that the condition disclosed in FIG. 7 will be obtained.

In this case there is provided in nozzle 32 a stopper 58 of a soft rubber material which is designed to be penetrated by a double-ended cannula 59 manually fitted to the nozzle by an attachment 60. This cannula is inserted into the blood vessel and then sleeve 53 is rotated in order to disengage it from pin 57. When the sleeve is released it will be displaced in relation to barrel 10' by means of spring 54, the plunger thereby being retracted or withdrawn in barrel 10' in order to draw the blood into container 30 in the manner described with reference to the embodiment disclosed in FIGS. 1 to 5, the movement of the plunger being accomplished automatically by means of spring 54, not manually as in FIGS. 1 to 5.

Once the container has been filled with blood the cannula may be removed from the nozzle. Stopper 58 will close automatically the passage through the nozzle. The container may be removed from the barrel manually in order to be transferred to a laboratory or to a storage freezer for future use.

The double-ended cannula 59 may be provided with well-known valve means (not shown) in order to close off the passage through the cannula when it is withdrawn from the container. Such valve means are disclosed e.g. in U.S. Pat. Nos. 3,469,572 to Nehring and 3,585,984 to Buchanan. Thus, several blood samples may be taken through one and the same cannula with only one penetration of the blood vessel.

It will be apparent to those skilled in the art that various modifications and variations could be made in the syringe of the invention and in the container forming part thereof without departing from the scope or spirit of the invention.

What is claimed is:

1. A syringe comprising an elongated barrel having an open discharge end, a plunger reciprocably mounted in the barrel, a container, means for removably engaging the container to the discharge end of the barrel to form the end wall thereof, said engaging means including a circumferential flange on said container, said flange having at least a flexible periphery for being flexed by the end of the barrel when the container is being engaged as the end wall thereof and for retaining said container as the end wall of the barrel by the tendency of at least said flexible periphery of the flange to restore to its unflexed state, and means on said barrel at said open end for flexing at least said flexible periphery and permitting restoration of said flange toward its unflexed state, said container having a substantially rigid first wall portion at the exterior side of the end wall and having an inside surface, and a flexible second wall portion at the interior side of the end wall and introvertible upon the inside surface of the first wall portion, said plunger having an end surface facing the container and designed to contact said second wall portion and to introvert the flexible wall portion upon the rigid wall portion during reciprocable movement of the plunger, said end surface being shaped to substantially conform to the shape of said inside surface of said first wall portion, and a nozzle on said first wall portion for attaching a hypodermic needle thereto.

2. A syringe as claimed in claim 1 wherein said flange is flexible and wherein said barrel includes a cylindrical socket at the discharge end thereof for receiving said flange and wherein said socket includes radially inwardly projecting means for receiving said flange by the flexing of the flange and for retaining said container in said socket during application of the piston on the flexible wall portion for introverting the latter upon the inside surface of the rigid wall portion.

3. A syringe as claimed in claim 2 wherein said flange includes a peripheral lip projecting from the edge of the flange at the side thereof which is opposite to said flexible second wall portion of the container, said lip having a conical outside surface the largest diameter of which is larger than the inside diameter of said socket, said lip yielding towards the container when inserted into the socket to frictionally engage the inner wall surface of the socket.

4. A syringe as claimed in claim 2 wherein said projecting means comprises a circumferential rib on the inside wall surface of the socket.

5. The syringe of claim 4 including means for permitting said end surface of said plunger to eject said container from said barrel upon further movement of said plunger toward said discharge end of said barrel after the introverting of said second wall portion upon the inside surface of the first wall portion.

6. The syringe of claim 4 wherein said container is prefilled before attachment to said barrel.

7. A syringe as claimed in claim 1 further comprising valve means controlling the passage between opposite sides of the plunger in the barrel to allow free flow of air from one side of the plunger to the other side thereof when the plunger is being displaced towards the discharge end of the barrel, and to prevent air flow between opposite sides of the plunger when it is displaced in the opposite direction, the interior of the barrel on the side of the plunger opposite to the discharge end of the barrel being vented to the atmosphere.

8. A syringe as claimed in claim 7 wherein said valve means comprises a sealing element on the plunger forming a conical lip thereon flared from a small end joining the plunger towards the end of the barrel which is opposite to the discharge end and engaging the inside wall surface of the barrel, said lip allowing air to pass between the plunger and the inside wall surface of the barrel when the plunger is being displaced towards the discharge end, and being forced to sealing engagement with said inside wall surface of the barrel when the plunger is being displaced in the opposite direction in the barrel.

9. A syringe as claimed in claim 7 wherein said syringe functions to fill said container and wherein said syringe includes interengaging abutment means on the plunger and the barrel for limiting the axial displacement of the plunger in the barrel during filling of said container for automatically filling the container to a predetermined extent.

10. A syringe as claimed in claim 9 wherein said abutment means on the plunger comprises several abutments at different axial positions spaced around the plunger, the barrel and the plunger being relatively rotatable to place said abutment means on the barrel in the moving path of any one of said several abutments at one time.

11. A syringe as claimed in claim 1 further comprising spring means between the plunger and the barrel biasing the plunger away from the discharge end of the barrel, and means for selectively retaining the plunger in a position in which said flexible second wall portion of the container is introverted by the piston to be collapsed against the inner surface of said one wall portion of the container.

12. A syringe as claimed in claim 11 wherein said retaining means are engaged and disengaged by relative rotation of the barrel and the plunger.

13. A syringe system comprising a syringe having an elongated barrel with an open discharge end, a plunger reciprocably mounted in the barrel, a plurality of disposable containers, means for removably attaching the containers individually to the discharge end of the barrel to form the end wall thereof, each said container having a substantially rigid first wall portion for forming the exterior side of the end wall and having an inside surface, and a flexible second wall portion at the interior side of the end wall and introvertible upon the inside surface of the first wall portion, said plunger having an end surface facing a container when attached to the barrel and designed to contact said second wall portion during the reciprocable movement of the plunger, said end surface being shaped to substantially conform to the shape of said inside surface of said first wall portion, anda nozzle on said first wall portion for attaching a hypodermic needle thereto, means for removably storing at least a portion of said plurality of containers and forming a bottom hole for each container for receiving the nozzle thereof and for closing the open end of the nozzle and thus the interior of the container to the atmosphere, said attaching means including flexible flange means on each of the containers and engagement means on the open end of the barrel, said engagement means capturing said containers individually by flexing said flexible flange means, the tendency of the flexible flange means to restore to its unflexed condition, retaining the container on the barrel for withdrawing the container from the storing means with the barrel.

14. The syringe of claim 2, including means for permitting said end surface of said plunger to eject said container from said barrel upon further movement of said plunger toward said discharge end of said barrel after the introverting of said second wall portion upon the inside surface of the first wall portion.

15. The syringe of claim 2 wherein said container is prefilled before attachment to said barrel.

16. A container arranged to be attached to a syringe, said container having a substantially rigid first wall portion, said first wall portion having an inside surface, a flexible second wall portion introvertible upon the inside surface of the first wall portion, and a nozzle on said first wall portion for attaching a hypodermic needle thereto, said container further comprising a flange on said first wall portion forming a peripheral lip which projects from the edge of the flange at the side thereof which is opposite to said flexible second wall portion of the container, said lip having a conical outside surface.

17. In a method for operating a syringe comprising an elongated barrel having an open discharge end, a plunger reciprocably mounted in the barrel for sealingly engaging the inner surface of the barrel as the plunger is displaced away from the discharge end, a container, means for removably attaching the container to the discharge end of the barrel to form the end wall thereof, said container having a substantially rigid first wall portion at the exterior side of the end wall and having an inside surface, and a flexible second wall portion at the interior side of the end wall and introvertible upon the inside surface of the first wall portion, said plunger having an end surface facing the container and shaped to substantially conform to the shape of said inside surface of said first wall portion, and a nozzle on said first wall portion for attaching a hypodermic needle thereto, wherein the means for removably attaching the container to the open end of the barrel includes a flexible flange on the containers for permitting retention of the container as the end wall of the barrel only by flexing interaction between the flange and the barrel and wherein the step of drawing the flexible second wall portion from a collapsed position in which it contacts and substantially conforms with said first wall portion, in order to draw liquid into said container through said nozzle, by displacing the plunger in the barrel away from the container and creating thereby a partial vacuum in the space of the barrel between the container and the plunger, by the sealing engagement of the plunger with the barrel.

18. The method as claimed in claim 17 further comprising the step of returning said flexible second wall portion towards said collapsed position by displacing the plunger towards the container, while venting the space in the barrel between the container and the plunger to the atmosphere, to bring said end surface of the plunger to contact said second flexible wall portion and to introvert it mechanically and positively upon the inside surface of said first wall portion in order to expel liquid drawn into the container through said nozzle.

* * * * *